Figure 1:
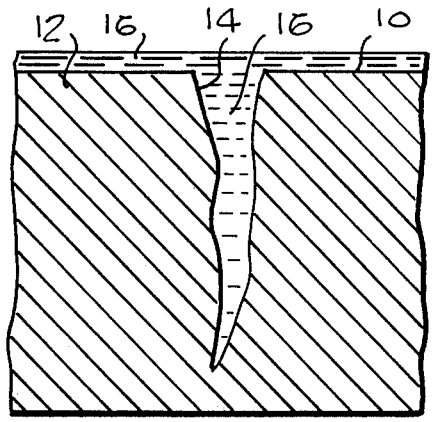

United States Patent [19]

Molina

[11] 3,981,185

[45] Sept. 21, 1976

[54] POSTEMULSIFIABLE DYE PENETRANT SYSTEM AND METHOD FOR USING SAME

[75] Inventor: Orlando G. Molina, Westminster, Calif.

[73] Assignee: Rockwell International Corporation, El Segundo, Calif.

[22] Filed: Dec. 23, 1974

[21] Appl. No.: 535,262

Related U.S. Application Data

[63] Continuation-in-part of Ser. No. 444,432, Feb. 21, 1974, Pat. No. 3,915,885, and a continuation-in-part of Ser. No. 444,433, Feb. 21, 1974, Pat. No. 3,915,886.

[52] U.S. Cl. ............................... 73/104; 23/230 R; 250/302; 252/301.19; 252/408
[51] Int. Cl.² ................. G01N 21/16; G01N 19/08; C09K 11/06
[58] Field of Search ..................... 252/408, 301.2 P; 73/104; 23/230 R; 250/302

[56] References Cited

UNITED STATES PATENTS

| | | | |
|---|---|---|---|
| 3,108,187 | 10/1963 | Thornbury | 252/301.2 P |
| 3,184,596 | 5/1965 | Alburger | 252/301.2 P |
| 3,558,882 | 1/1971 | Fijalkowski | 73/104 X |
| 3,564,249 | 2/1971 | Molina | 252/301.2 P |
| 3,716,492 | 2/1973 | Graham et al. | 252/408 X |
| 3,896,664 | 7/1975 | Alburger | 252/408 X |

*Primary Examiner*—Benjamin R. Padgett
*Assistant Examiner*—David Leland
*Attorney, Agent, or Firm*—Charles T. Silberberg; L. Lee Humphries

[57] ABSTRACT

Postemulsifiable dye penetrant inspection system and method employing substantially biodegradable dye penetrant compositions and emulsifiers, for use in non-destructive testing of objects to locate voids and defects therein, the dye penetrant composition consisting essentially of an organic dye, preferably a fluorescent dye, and a carrier or solvent for said dye, in the form of certain straight chain, primary, aliphatic oxyalkylated alcohols, particularly biodegradable surfactants comprised of the nonionic condensation products of linear primary aliphatic alcohols having from 10 to 18 carbon atoms, with ethylene oxide and propylene oxide, preferably in the form of a mixture thereof, or in the form of certain ethoxylated secondary alcohols, particularly the biodegradable nonionic surfactants comprised of ethoxylates of a mixture of secondary alcohols having linear alkyl chains of from 11 to 15 carbon atoms, such surfactants and the resultant dye penetrants having limited water solubility and normally requiring large amounts of water at high pressure for removal of excess dye penetrant from the object surface. An emulsifier is thus employed to treat the penetrant covered object surface and to remove excess dye penetrant, such emulsifier also comprised of the above noted classes of biodegradable nonionic surfactants, but of a composition or nature which are highly soluble and which facilitate removal of the resulting emulsified dye penetrant with water as by spraying.

In the method of application of the posemulsifiable dye penetrant system of the invention, the dye penetrant composition is applied to the surface of an object containing cracks and flaws, the object is contacted, as by immersion, with the emulsifier noted above, and water is applied, as by spraying, to the emulsified penetrant on the surface of the object, without removing dye penetrant from the cracks and defects, and with or without a developer, the surface of the object is viewed under suitable lighting conditions, e.g., ultraviolet or black light when the dye in the penetrant is a fluorescent dye, to locate any cracks or defects in the surface of the body as indicated by colored traces from the dye penetrant remaining in the cracks and flaws.

19 Claims, 4 Drawing Figures

POSTEMULSIFIABLE DYE PENETRANT SYSTEM AND METHOD FOR USING SAME

This application is a continuation-in-part of my copending applications Ser. Nos. 444,432, now U.S. Pat. No. 3,915,885, and 444,433, now U.S. Pat. No. 3,915,886, both filed Feb. 21, 1974.

BACKGROUND OF THE INVENTION

This invention relates to an improved postemulsifiable dye penetrant system and method for non-destructively testing material specimens to locate and identify surface voids, cracks or defects, and more particularly to an improved system and method as described above employing therein certain combinations of biodegradable nonionic dye penetrants and biodegradable nonionic emulsifiers. The invention is especially concerned with a postemulsifiable dye penetrant inspection system and method employing stable and sensitive dye penetrant compositions of the above type having the characteristics of being able to disclose a wide range of defective conditions in parts, employing as solvent or vehicle essentially a biodegradable nonionic surfactant in the form of certain combinations or mixtures of certain oxyalkylated alcohols, and also employing emulsifiers for such dye penetrant compositions, containing a biodegradable nonionic surfactant of the general type employed in the dye penetrant, but having a higher degree of water washability, to permit rapid removal of the emulsified dye penetrant by application of water.

In known penetrant inspection methods for rapid location and evaluation of surface flaws or cracks in test bodies or parts, a dye penetrant composition, preferably containing a fluorescent dye, and which will penetrate the openings of the surface cracks or flaws in the part, is applied to the surface of the test body, and the excess penetrant composition is removed from the surface of the body. A developer composition may then be applied to the part surface, which acts as a wick and causes the liquid penetrant containing the fluorescent dye, which was retained in the cracks or surface flaws, to be drawn up out of the surface defects by capillary action. The part is then exposed to appropriate lighting conditions such as invisible fluorescigenous light, and the location of the surface flaws is revealed by the emission of visible fluorescent light by the penetrant dye which was retained in the cracks or flaws after the penetrant composition was removed from the surface of the part.

For best efficiency, particularly for the detection and location of minute surface cracks and flaws, as well as intermediate size and gross cracks, it is necessary that the dye penetrant composition have high sensitivity.

Volatile type solvents are commonly employed for extending or thinning dye penetrant inspection solutions or compositions. This is done chiefly for the purpose of lowering the viscosity of the penetrant in order to adapt it for application in spraying systems. Thus for example solvents such as kerosene, light fuel oils, and methyl ethyl ketone, all highly volatile solvents, have heretofore been employed in prior art dye penetrants. See for example U.S. Pat. No. 2,806,959. Further, most dye penetrant solutions in practice generally require the use of a combination of solvents, including primary and secondary solvents, extender solvents and wetting agents.

However, the use of volatile solvents in dye penetrant compositions has certain disadvantages. Thus, the use of volatile solvents in dye penetrants results in the evolution of fumes and solvent vapors which are rapidly formed by the evaporating solvent.

Since the use of organic solvents as noted above in the dye penetrant composition does not render the excess dye penetrant composition readily removable from the surface of the part by water, an emulsifier is often applied over the dye penetrant applied to the surface of the part, to render the emulsified excess dye penetrant water washable, followed by removal of the emulsified penetrant with a water wash.

In these dye penetrant systems an additional criterion has recently been developed with respect to both the dye penetrant solutions and emulsifiers. Generally dye penetrant solutions and emulsifiers presently employed and containing solvents and wetting agents present a disposal problem in that they generally contain petroleum solvents and oils which are substantially non-biodegradable, that is, they are very difficult to decompose by bacteria and sewage disposal plants, and constitute serious polluters. Hence the necessity for the development of dye penetrant solutions and emulsifiers for use in a postemulsifiable dye penetrant inspection system, which penetrant solutions and emulsifiers employ dye solvents and carriers which are biodegradable, and are readily available despite the petrochemical shortage, and which render the emulsified penetrant readily water washable, has attained considerable importance.

U.S. Pat. No. 3,716,492 discloses a liquid penetrant composition consisting essentially of a major amount of methyl ester of a fatty acid, such as Methyl Sperm, and which is essentially water insoluble, and a minor amount of a nonionic surfactant such as polyethoxylates of secondary linear alcohols, the methyl ester being the principal liquid vehicle and the nonionic surfactant functioning to emulsify the methyl ester to form a water base emulsion, the methyl ester and nonionic surfactant being biodegradable.

In my above copending applications there are disclosed novel dye penetrant compositions having improved sensitivity characteristics, and which are biodegradable, containing as the sole vehicle for the dye, certain biodegradable nonionic oxyalkylated alcohols. Although dye penetrants of this type have been tested extensively and have proved highly satisfactory and effective for most applications, certain of these formulations having high sensitivity, and containing certain of the above noted oxyalkylated alcohols as surfactant, require employment of relatively high volumes of water and increased pressure to wash excess penetrant from the surface of the test specimen.

Accordingly, an object of the present invention is the provision of a postemulsifiable dye penetrant inspection system and method employing dye penetrant solutions or compositions of the type noted above and described in my above copending applications, and employing certain types of the oxyalkylated alcohols described therein as surfactant, such dye penetrant compositions being biodegradable and having high sensitivity, in conjunction with a postemulsifier which when applied to the dye penetrant, permits ready washability of the emulsified dye penetrant with a reduced volume of water and at reduced pressure as compared to that which would ordinarily be required for removing such dye penetrant composition in the absence of the emulsifier. A particular object of the invention is to provide a postemulsifiable dye penetrant inspection system and method of the above noted type, and which employs as a sole liquid carrier or vehicle for the dye penetrant and as emulsifier, readily available and biodegradable nonionic surfactants of the type disclosed in my above copending applications, and which particularly render the emulsified dye penetrant easily removable employing modest volumes of water at normal washing pressures.

DESCRIPTION OF THE INVENTION

The above objects and advantages can be accomplished according to the invention, and an improved postemulsifiable dye penetrant inspection method and system employing biodegradable nonionic surfactants provided, by treatment of a specimen or object whose surface conditions are to be inspected, with a postemulsifiable dye penetrant containing as carrier for the dye, e.g., fluorescent dye, certain biodegradable nonionic surfactants comprised of certain oxyalkylated alcohols in the form of condensation products of certain linear primary aliphatic alcohols with ethylene oxide and propylene oxide, or of ethoxylates of certain linear secondary aliphatic alcohols, separately or in admixture, followed by treatment of the penetrant covered object with an emulsifier containing as essential component biodegradable nonionic surfactants of the same general class as employed as carrier for the dye in the dye penetrant composition, but having greater water solubility. The invention process permits use of certain biodegradable nonionic surfactants of the general type noted above and described in detail hereinafter, which confer high sensitivity on the dye penetrant but which have limited water solubility and rendering the dye penetrant difficult to wash away with water, and hence would require substantial volumes of high pressure water for removal of excess dye penetrant, together with an emulsifier containing biodegradable nonionic surfactants of the same general type as employed in the dye penetrant, but of a somewhat different chemical composition and which are essentially water soluble, so that when the emulsifier is applied to the dye penetrant on the surface of the object, it readily combines with the penetrant on the object surface, and does not penetrate into the cracks or flaws in the surface of the object, and the emulsified penetrant on the object surface can be readily removed employing substantially lower volumes of water at normal water pressure. For this purpose, as will be pointed out in further detail below, the second surfactant in the emulsifier has a higher number of oxyalkyl groups in the hydrophilic portion than the first surfactant in the dye penetrant composition.

Thus there is provided according to the invention a postemulsifiable dye penetrant process which permits the employment in both the dye penetrant and the emulsifier of biodegradable nonionic surfactants which are unusually fast acting and stable, providing excellent defect-revealing sensitivity and affording brilliant indications of surface defects and cracks, such dye penetrants generally having an extremely high flash point, e.g., in excess of 400°F., are compatible and noncorrosive to most structural metals such as steel, aluminum, and titanium, and are odorless, in conjunction with highly effective emulsifiers for such dye penetrants, both the dye penetrants and emulsifiers being completely biodegradable and avoiding pollution of the delicate bacterial balance of sewage systems.

The dye penetrant compositions employed in the process of the present invention otherwise have substantially the same improved properties and advantages of the dye penetrants of my above copending applications, in that they do not require the presence of any additional vehicles, volatile or nonvolatile solvents, or wetting agents, generally employed in prior art dye penetrant solutions and compositions. This is in contrast, for example, to the above U.S. Pat. No. 3,716,492 which employs as its principal liquid vehicle a methyl ester of a fatty acid. The employment of such dye penetrant compositions containing the above described nonionic surfactant as the essential and sole vehicle in conjunction with the emulsifier compositions, according to the invention permit instant washability of the emulsified dye penetrant from the surface of parts to be inspected without loss of dye penetrant solution entrapped within the defects and cracks.

The nonionic biodegradable solvent or carrier employed essentially as the sole vehicle for the dye of the dye penetrant composition according to the invention can be alkylene oxide condensation products prepared by the reaction of an organic compound having a reactive hydrogen atom, such as an aliphatic alcohol, with ethylene oxide, propylene oxide, or mixtures thereof. More particularly, one class of such nonionic solvents or carriers can be defined as straight chain, primary, aliphatic oxyalkylated alcohols, generally in the form of mixtures thereof, wherein the primary aliphatic alcohols can have from 8 to 20 carbon atoms, preferably 10 to 18 carbon atoms, and the oxyalkyl groups are ethylene oxide and propylene oxide, preferably in the form of a mixture thereof.

One class of nonionic carriers within the broad class of materials defined above is a cogeneric mixture of compounds represented by the formula:

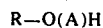

R—O(A)H wherein:

R is an essentially linear alkyl group having from 10 to 18 carbon atoms, with the proviso that at least 70 weight percent of said compounds in said mixture have an R of from 12 to 16 carbon atoms, and A is a mixture of oxypropylene and oxyethylene groups, said oxypropylene and oxyethylene groups being from 55% to 80% of the total weight of the compounds, the oxypropylene to oxyethylene ratio of said total weight being from 0.85:1 to 2.75:1, preferably 1.25:1 to 2.25:1.

Another preferred class of condensation products or oxyalkylated alcohols within the above definition are those wherein the aliphatic alcohols of the oxyalkylated alcohols, or R in the above formula, ranges from 12 to 18 carbon atoms, and the total number of ethylene oxide and propylene oxide groups in the mixture thereof, or designated A in the above formula, ranges from about 4 to about 14.

The term "cogeneric mixture" as employed herein, designates a series of closely related homologues obtained by condensing a plurality of oxide units, with an alcohol or a mixture thereof. As is known, when a mixture of this type is generated, various oxyalkylene chain lengths are obtained.

Alcohols which may be employed in the preparation of the products noted above are those essentially linear, primary, aliphatic alcohols having from 8 to 20 carbon atoms, preferably 10 to 18 carbon atoms. Mixtures of alcohols are usually preferred since their use provides for a good balance of properties in the resulting products. Examples of alcohols which are operable include decyl alcohol, undecyl alcohol, lauryl alcohol, tridecyl alcohol, tetradecyl alcohol, pentadecyl alcohol, cetyl alcohol, heptadecyl alcohol, stearyl alcohol, hydrogenated tallow alcohol, and mixtures thereof. They may be naturally-derived such as from coconut oil or synthetically-derived such as from linear alkanes or linear olefins.

The nonionic biodegradable surfactants employed as carrier or vehicle for the dye of the penetrant solution according to the invention, are prepared by condensing an alcohol or mixture of alcohols, as described above, with a mixture of ethylene oxide and propylene oxide, in the presence of an alkaline catalyst, such as potassium hydroxide. The oxide mixture may be added to the alcohol in one continuous step or it may be added in several steps. The products thus produced possess random distribution of oxyethylene and oxypropylene groups.

The nonionic surface active agents described above and their method of preparation are disclosed in U.S. Pat. No. 3,504,041, and such disclosure is incorporated herein by reference. These surface active agents are believed to include, for example, that class of surfactants which are marketed as the "Plurafac" surfactants "RA-40" grades.

Another class of biodegradable liquid, water miscible oxyalkylated alcohol condensation products within the above definition are those wherein the aliphatic alcohol, or R, is a straight chain alkyl group having from 8 to 20 carbon atoms, the number of ethylene oxide groups in the mixture thereof with propylene oxide, or A, ranges from 3.75 to 12.75, and the number of propylene oxide groups in such mixture ranges from 1.7 to 7.0, the oxyethylene to oxypropylene ratio in such mixtures being from 1.8:1 to 2.2:1. Such cogeneric mixtures can be prepared in two steps, the first step being condensation of an alcohol mixture and ethylene oxide in the presence of an alkaline condensing agent or catalyst, to form an ethoxylated product, followed by condensing the resulting ethoxylated product with propylene oxide. There can be employed in such reaction a mixture of straight chain aliphatic alcohols having from 8 to 20 carbon atoms in the aliphatic chain. This cogeneric mixture of condensation products and the method of their preparation are disclosed in U.S. Pat. No. 3,340,309, and such disclosure is also incorporated herein by reference. The nonionic oxyalkylated alcohols marketed as the "RA-20" grades of "Plurafac", are believed representative of the class of surface active agents disclosed in the latter patent.

Various other Plurafac grades which are marketed and are believed to be generally within the above-described classes of oxyalkylated alcohol surfactants are those designated RA-43, A-24, A-25, B-25-5, B-26 and D-25.

A class of particularly preferred nonionic biodegradable solvents or carriers which can be employed as substantially the sole vehicle for the dye of the dye penetrant compositions according to the present invention are ethoxylates of a mixture of linear secondary aliphatic alcohols, with the hydroxyl groups randomly distributed, the linear aliphatic hydrophobic portion of such alcohols being a mixture of alkyl chains containing in the range from 10 to 17 carbon atoms, preferably from 11 to 15 carbon atoms, and containing an average of from 3 to 12 moles of ethylene oxide.

The above particularly preferred class of nonionic biodegradable surfactant employed as carrier for the dye penetrant of the invention is a mixture of compounds which can be represented by the formula:

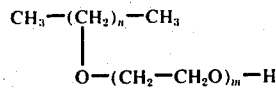

where $n$ is in the range from 9 to 13, and $m$ is 3 to 12.

The linear alkyl hydrophobic portion of the above defined surfactant is a mixture of $C_{11}$ to $C_{15}$ linear alkyl chains, and can be derived from a mixture of $C_{11}$ to $C_{15}$ aliphatic secondary alcohols, for example the secondary undecyl, dodecyl, tridecyl, tetradecyl and pentadecyl alcohols. The hydrophilic portion of the surfactant is a polyoxyethylene chain randomly attached to any carbon atom of the linear alkyl hydrophobic chains, other than to the terminal carbon atoms thereof, through an ether linkage. It will accordingly be understood that the specific carbon atom in the alkyl hydrophobic chains to which the hydrophilic polyoxyethylene chain is attached will become a -CH - group. Such hydrophilic polyoxyethylene chain is generally expressed in terms of an average number of moles of ethylene oxide.

Illustrative examples of biodegradable nonionic surfactants of the types defined in the above formula are those consisting of a mixture of ethoxylates of from 11 to 15 carbon atoms in the aliphatic hydrophobic chain, and which have an average of 3, 5, 7, 9 and 12 moles of ethylene oxide, respectively, as the hydrophil.

Materials corresponding to these five examples of biodegradable nonionic surfactants are marketed, respectively as:

| | |
|---|---|
| Tergitol | 15-S-3 |
| Tergitol | 15-S-5 |
| Tergitol | 15-S-7 |
| Tergitol | 15-S-9 |
| Tergitol | 15-S-12 |

In each case of the Tergitol S series of surfactants listed above, the number to the left of the S indicates a hydrophobic aliphatic chain of from 11 to 15 carbon atoms derived from a mixture of alcohols on $C_{11}$ to $C_{15}$ backbone chains, and the number to the right of the S designates the average number of moles of ethylene oxide as the hydrophil. Thus for example, Tergitol 15-S-5 is a mixture of linear aliphatic alcohols in the $C_{11}$ to $C_{15}$ range ethoxylated with an average of 5 moles of ethylene oxide. All of these commercially marketed Tergitol S series of surfactants are water soluble except for Tergitol 15-S-3, which is essentially water insoluble. Mixtures of these materials can also be employed in providing the dye penetrant of the invention, such as a mixture of the above Tergitols 15-S-5 and 15-S-3.

The above preferred class of nonionic biodegradable surfactants employed as carrier or vehicle for the dye of the penetrant solution according to the invention, are prepared by reacting an alcohol or mixture of alcohols, as described above, with the desired proportion of ethylene oxide, in the presence of an alkaline catalyst, such as potassium hydroxide. The ethylene oxide may be added to the alcohol or mixture of alcohols in one continuous step or it may be added in several steps. The products thus produced possess random distribution of oxyethylene groups, as noted above.

Another process for preparing the above nonionic surfactants in the form of ethoxylates of linear secondary aliphatic alcohols, is described in U.S. Pat. No. 2,870,220.

Any suitable dye generally employed in dye penetrant compositions can be incorporated into the nonionic oxyalkylated alcohol surfactants described above for producing the dye penetrant compositions employed in the invention process. Preferably, however, a fluorescent dye is employed for this purpose. The oxyalkylated surfactant vehicle for the dye is compatible therewith and has the ability to dissolve either small or relatively large amounts of the dye and to hold a high concentration of dye in solution while providing good resolution and clarity of the dye trace in the cracks and flaws.

As previously noted, the dye penetrant solution employed according to the invention preferably contains a fluorescent dye. Various types of fluorescent dyes can be employed including for example the dye marketed as Fluorol 7GA as well as other fluorescent dyes such as those marketed as Calcofluor Yellow, Azosol Brilliant Yellow 6GF; Rhodanine B, Rhodanine 6 GDN, Calcofluor White RW, Blancophor White AW, Auramine and Eosine G, and water soluble fluorescent dyes such as Blancophor FFG.

The dye penetrant composition employed according to the invention alternatively can contain non-fluorescent or daylight type dyes such as azo type dyes, e.g., xyleneazo-beta-naphthol, Mefford No. 322 dye, believed to be o-toluene-azoxyleneazo-beta-naphthol, and the azo dyes marketed as Oil Red O and Sudan Red. These dyes conveniently can be employed where daylight or white light is only available, and particularly where the surface of the body to be detected contains relatively gross cracks. However, it is preferred to employ fluorescent dyes having greater sensitivity or detectability as result of the high contrast obtained by the fluorescent indications.

If desired, small amounts of extenders such as kerosene, and volatile solvents such as methyl ethyl ketone, isopropyl alcohol, and the like, and water, can be added to the dye penetrant composition of the invention containing the oxyalkylated alcohol carrier, to vary the properties thereof. It is noted however that in preferred practice these additives are not employed and in effect a "one liquid" solution is provided according to the invention, in which the oxyalkylated alcohol surfactant is essentially the sole carrier for the dye. Also, if desired, corrosion inhibitors such as, for example, morpholine, can be added in a small amount such as 0.01 to 0.1% by volume of the dye penetrant composition, particularly where the object being tested is highly susceptible to corrosion, such as magnesium.

The amount of dye which is incorporated into the oxyalkylated alcohol surfactant or carrier to produce the dye penetrant composition of the invention, can range from about 0.1 to 15, preferably about 0.5 to about 10, parts of the dye, or mixtures thereof, per 100 parts of the oxyalkylated alcohol surfactant, by weight. In preparing the dye penetrant composition employed according to the invention, the dye is simply added to the oxyalkylated alcohol carrier, in the desired proportion. The resulting dye penetrant composition has both high and low temperature stability.

Where a developer composition is employed, any one of the three general types of developer compositions, namely, dry powder, wet aqueous (water-base) and wet nonaqueous (volatile solvent base) developer compositions can be employed. In each case, the developer composition contains a light colored powder, forming a coating which contrasts with the color of the dye in the penetrant and which acts as a wick or blotter, and causes liquid penetrant containing the dye, e.g. fluorescent dye, which was retained in the cracks or surface flaws, to be drawn up out of the surface defects by capillary action and to "bleed" through the powder. Preferred developer compositions for use in conjunction with the dye penetrant composition according to the invention, are those described in my U.S. Pat. No. 3,803,051, which is a dry powder developer containing fumed alumina, fumed silica, fumed titanium dioxide and talc, and in my U.S. Pat. No. 3,748,469, and which is a wet nonaqueous developer composition consisting essentially of isopropyl alcohol, talc and glycol monobutyl ether. The descriptions of such developer compositions contained in the above patents are incorporated herein by reference.

The dye penetrant composition employed in the invention process, employing the above biodegradable nonionic oxyalkylated alcohol surfactants can be tailored to have varying degrees of sensitivity for detection of the smallest microcracks to gross cracks in a part surface by generally varying the amount of dye incorporated, and also by selecting particular surfactants or combinations thereof. This is illustrated by the compositions I to IV below, containing Tergitol 15-S-3 as sole vehicle:

TABLE 1

| COMPONENTS | COMPOSITIONS (parts by weight) | | | |
| | I | II | III | IV |
| | Sensitivity Level | | | |
| | Super High | High | Medium | Low |
| Tergitol 15-S-3 | 100.0 | 100.0 | 100.0 | 100.0 |
| Calcofluor White RW | 5.0 | 2.5 | 1.25 | 0.675 |
| Fluorol 7GA | 1.5 | .75 | .375 | 0.187 |

Composition I particularly is a super high sensitivity dye penetrant composition which requires a more rigorous water wash than somewhat less sensitive dye penetrant compositions employing other related above described Tergitols, due to the presence therein of the above noted specific Tergitol 15-S-3, which is less water soluble or has lower water solubility than corresponding Tergitols. As matter of fact, Tergitol 15-s-3 is substantially water insoluble. Thus, although composition I is particularly advantageous for inspection of parts having a very smooth surface with microcracks, and compositions II, III and IV are also highly advantageous for inspection of parts having cracks of intermediate size and gross cracks, due to the substantially reduced water solubility of the Tergitol 15-S-3, large volumes of high pressure water are needed to remove excess dye penetrant from the surface of a part to which the penetrant has been applied, when employing compositions I to IV.

Corresponding dye penetrant compositions to those of Table 1 can be made by substituting Plurafac A-24, for example, for the Tergitol 15-S-3 therein.

The invention process will be more clearly understood from the further description below taken in connection with the accompanying drawing wherein FIGS. 1 to 4 illustrate the steps in the invention process.

Referring to the drawing, FIG. 1 illustrates application of the biodegradable substantially non water soluble penetrant, e.g. composition I, to the surface 10 of a part 12 containing cracks such as illustrated at 14. It will be seen that the dye penetrant solution 16 is contained on the part surface 10 and in the cracks 14.

Figure 2:
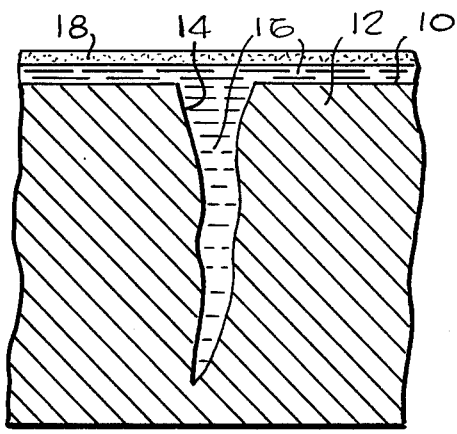

Viewing Fig. 2, according to the postemulsifying penetrant process of the invention, there is then applied over the dye penetrant composition on the part surface, an emulsifier 18 to render the emulsified penetrant easily water washable. Such emulsifiers have as essential component a biodegradable nonionic surfactant, e.g., of the same class as the particular Tergitol of composition I, or the particular Plurafac of the corresponding dye penetrant composition. Thus, as a general rule, for greater sensitivity of the dye penetrant, where a dye penetrant composition is employed containing nonionic biodegradable surfactants in the form of ethoxylates of linear secondary aliphatic alcohols, as represented by the above Tergitols, there can be employed in the dye penetrant composition, surfactants of this type containing from 3 to 4 ethylene oxide groups, which are of low water solubility or which with respect to Tergitol 15-S-3, specifically, are essentially water insoluble, as represented by Compositions I to IV above, in conjunction with an emulsifier consisting essentially of the same class of nonionic biodegradable Tergitol-type surfactants which contain from 5 to 12 moles of ethylene oxide or ethylene oxide groups, and which are essentially water soluble. Similarly, the above defined Plurafac type surfactant, e.g., formed of a mixture of straight chain, primary, aliphatic oxyalkylated alcohols, and wherein about 4 to about 8 total ethylene oxide and propylene oxide groups are present, as represented by the material marketed as Plurafac A-24, and which are of comparatively lower water solubility, can be employed in conjunction with an emulsifier consisting essentially of the same general class of Plurafac noted above, but wherein the total number of ethylene oxide and propylene oxide groups can range from about 9 to about 14, and which are of greater solubility.

Thus, for example, where Plurafac A-24, which is understood to contain a total number of ethylene oxide and propylene oxide groups ranging from about 4 to about 8, is employed as carrier in providing a high sensitivity dye penetrant composition, an emulsifier can be employed containing the same general class of Plurafacs but wherein the total number of ethylene oxide and propylene oxide groups ranges from about 9 to about 14, e.g. as represented by Plurafac A-25. Similarly, where, for example, Tergitol 15-S-3 is employed as carrier for the dye in the dye penetrant composition, an emulsifier can be employed containing from about 5 to about 12 moles of ethylene oxide, e.g., Tergitol 15-S-5, 15-S-7, 15-S-9 or 15-S-12, separately or in combinations of one or more of such Tergitols, e.g., a combination of Tergitols 15-S-5 and 15-S-9, a combination of Tergitols 15-S-5 and 15-S-7, or a combination of Tergitols 15-S-9 and 15-S-12, the respective Tergitols in each such combination being employed in varying ratios of from about 5 to about 95% by volume.

Figure 3:
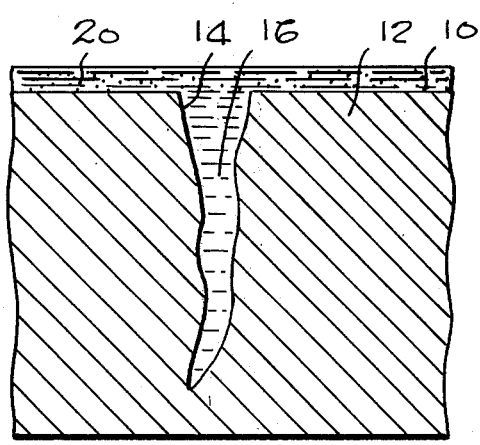

The object or part to which the dye penetrant composition has been applied is contacted with the above described emulsifiers in any desired manner as by spraying with or by immersion in the emulsifier, for a relatively short period of time, e.g., about 1 to 5 minutes. Referring to FIG. 3 of the drawing, the spontaneous mixing of both the emulsifier 18 and the dye penetrant solution 16 on the part surface forms a water soluble biodegradable mixture 20 which does not penetrate into the cracks 14 which contain dye penetrant solution 16.

Figure 4:
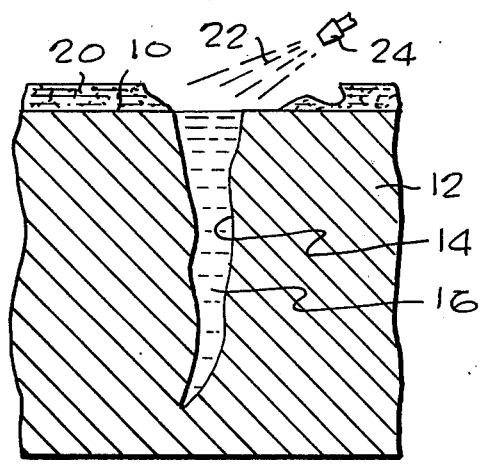

Referring to FIG. 4 of the drawing, the resulting emulsified penetrant 20 on the surface of the object is then contacted with water in any suitable manner as by spraying the water at 22 from a water spray nozzle 24, to remove the excess emulsified dye penetrant 20 from the part surface without removing dye penetrant 16 trapped in the cracks and flaws 14 in the surface of the object. The part is then dried, for example, by a blast of air. If desired, as noted above, but not necessarily, the part 12 can then be covered with a developer, e.g. a dry powder, aqueous or non-aqueous developer, and the developer allowed to dwell on the surface for a short period, e.g. about 1 to 3 minutes. Excess developer is then removed from the surface of the part. The part is then viewed under suitable lighting conditions, e.g., black light or fluorescent light where a fluorescent dye has been employed in the dye penetrant composition, for indication of the defects and cracks in the part.

The following are examples of practice of the invention but are not limitative of the benefits and advantages obtained by practice of the invention.

EXAMPLE 1

The fluorescent dye penetrant composition I of Table 1 above, containing biodegradable Tergitol 15-S-3 as carrier, was applied as by spraying to a chromium-plated brass test panel containing minute cracks of the order of 0.00002 to 0.0001 inch in width, closely distributed over its entire surface.

The test panel covered with the dye penetrant was then immersed in biodegradable Tergitol 15-S-9 as emulsifier and allowed to remain immersed in the emulsifier for a period of about 1 minute. The test panel containing the emulsified penetrant was then sprayed with water applied by an air-water spray over the dry penetrant-emulsifier coating, causing instantaneous washing away of the emulsified dye penetrant on the surface of the panel without dislodging the dye penetrant from the surface cracks and thus entrapping the penetrant therein.

The test panel was then covered with a powder developer having the following composition, according to my above U.S. Pat. No. 3,083,051.

| COMPONENTS | Percent by Weight |
| --- | --- |
| Talc | 52 |
| Alumina | 35 |
| Silica | 4 |
| TiO$_2$ | 9 |

The above developer was permitted to dwell over the surface of the test panel for a period of about 2 minutes.

Excess developer composition was then carefully removed from the surface of the test panel by means of a gentle air blast.

The panel was then placed under black light (fluorescent) illumination and the above treated surface of the panel viewed in such illumination. It was observed that the panel surface disclosed fluorescent indications from numerous readily defined microcracks therein, such fluorescent indications being sharp and brilliant and revealing all defective conditions on the surface of the test panel.

EXAMPLE 2

The procedure of Example 1 was repeated but without treatment of the dye penetrant covered surface of the test panel with any emulsifier. Thus, following application of the dye penetrant composition I to the surface of the test panel, a water wash was applied as by an air-water spray over the coating of the dye penetrant composition I on the test panel, followed by application of the developer to the surface of the penetrant.

It was found that a vigorous water wash requiring large volumes of water at a pressure of about 80 – 100 psi and an extended period of washing of about 4 to 5 minutes, was required in order to substantially completely remove excess dye penetrant composition from the surface of the test panel, prior to application of the developer.

EXAMPLE 3

The procedure of Example 1 was repeated but employing an aluminum test panel containing microcracks, and wherein the emulsifier was Tergitol 15-S-5.

Excellent results were obtained comparable to those obtained in Example 1.

EXAMPLE 4

The procedure of Example 1 was repeated but employing in place of composition I, a similar composition but employing Plurafac A-24 as dye solvent or carrier. Also, in place of the Tergitol 15-S-9 emulsifier employed in Example 1, the emulsifier used was Plurafac A-25, comprised of a straight chain, primary aliphatic oxyalkylated alcohol mixture believed to contain about 12 to about 18 carbon atoms in the alcohol chains, and a total of from about 9 to 14 oxyethylene and oxypropylene groups, as described above.

Bright fluorescent indications of the cracks and defects in the surface of the panel were obtained similar to the results achieved in Example 1.

EXAMPLE 5

A test on an aluminum panel having cracks of intermediate size was carried out following the procedure of Example 1, but utilizing composition III of Table 1, containing Tergitol 15-S-3, and employing as emulsifier a mixture of approximately equal parts by volume of Tergitol 15-S-5 and Tergitol 15-S-9.

Excellent results with respect to water washability of the penetrant emulsified surface of the panel, as well as excellent brilliant indications of the defects on the surface of the test panel, were achieved.

EXAMPLE 6

The procedure of Example 1 was essentially followed, but employing in place of composition I a non-fluorescent dye penetrant solution consisting of 15 parts of Tergitol 15-S-3 and 1 part of Oil Red O dye, by volume.

Excellent results of crack detectability were obtained employing such non-fluorescent dye penetrant. However, the brightness and sensitivity of the colored dye traces obtained employing the non-fluorescent dye penetrant of this example were not as great as for the fluorescent dye penetrant composition I of Example 1.

EXAMPLE 7

The procedure of Example 1 was followed except that in place of the powder developer employed in Example 1, a nonaqueous developer having the following composition according to my above U.S. Pat. No. 3,748,469 was employed:

| COMPONENTS | Percent by Weight |
| --- | --- |
| Isopropyl alcohol | 70.5 |
| Talc | 28.6 |
| Glycol monobutyl ether | 0.9 |

The above developer was permitted to remain on the panel surfaces to which it was applied for a period of 2 minutes, until substantially all of the isopropyl alcohol had evaporated and a substantially dry powder coating was formed.

Results similar to the results of Example 1 were obtained.

In all of Examples 1 to 7 above, all of the dye penetrants and the emulsifiers were biodegradable and hence avoided pollution of the sewage disposal systems into which they were discharged.

From the foregoing, it is seen that the invention provides a highly effective postemulsifiable penetrant inspection system and method employing as sole carrier or vehicle in the dye penetrant, and as essential component of the emulsifier, certain oxyalkylated alcohol biodegradable nonionic surfactants, and permitting substantially instantaneous removal of emulsified dye penetrant from the surface of the part in a single wash operation employing modest amounts of water at normal water pressure, while maintaining the dye penetrant in the cracks or defects of the part, followed by further processing as desired in the conventional manner for viewing under suitable, e.g., fluorescent lighting conditions, to obtain highly brilliant dye traces from cracks and flaws in the part surface. The dye penetrants and emulsifiers employed according to the invention afford substantially non-flammable high performance dye penetrant compositions having a wide range of sensitivity and non-flammable emulsifiers providing improved water washability characteristics of the resultant emulsified penetrant. The dye penetrants and emulsifiers employed according to the invention process avoid the use of volatile extenders and thinners.

Since various changes and modifications of the invention will occur to and can be made readily by those skilled in the art without departing from the invention concept, the invention is not to be taken as limited except by the scope of the appended claims.

I claim:

1. A postemulsifieable dye penetrant inspection method for detecting cracks and flaws in the surface of an object, which comprises applying to said surface a biodegradable liquid dye penetrant composition which consists essentially of (1) a first biodegradable nonionic surfactant consisting essentially of an oxyalkylated alcohol, or a mixture thereof, and (2) a small amount of a dye soluble in said first surfactant, said first surfactant having limited water solubility and rendering the dye penetrant difficult to wash away with water, contacting the dye penetrant covered surface of said object with an emulsifier containing as essential component a second biodegradable nonionic surfactant consisting of an oxyalkylated alcohol, or a mixture thereof, said second surfactant being essentially water soluble, and rendering the emulsified penetrant water washable, said first and second biodegradable nonionic surfactants being of the group consisting of (a) straight chain, primary, aliphatic oxyalkylated alcohols, wherein said alcohols can contain from 8 to 20 carbon atoms and the oxyalkyl groups are a mixture of ethylene oxide and propylene oxide groups, and (b) ethoxylates of linear secondary aliphatic alcohols, with the hydroxyl groups randomly distributed, the linear aliphatic portion of said alcohols being a mixture of alkyl chains containing in the range from 10 to 17 carbon atoms, and containing an average of from 3 to 12 moles of ethylene oxide, said second surfactant in the emulsifier having a higher number of oxyalkyl groups in the hydrophilic portion than said first surfactant, contacting the emulsified penetrant on the surface of said object with water and removing said dye penetrant from said surface without removing said dye penetrant composition from said cracks and flaws in said surface, and viewing the surface of said object under lighting conditions to obtain colored traces from the dye in said cracks and flaws.

2. A method as defined in claim 1, wherein said first nonionic surfactant in the dye penetrant composition is the sole liquid carrier for the dye therein.

3. A method as defined in claim 1, wherein said surfactant (a) is a mixture of compounds having the formula:

wherein R is an essentially linear alkyl group having from 10 to 18 carbon atoms, at least 70 weight percent of said compounds in said mixture having an R of from 12 to 16 carbon atoms, and A is a mixture of oxypropylene and oxyethylene groups, said oxypropylene and oxyethylene groups being from 55 to 80% of the total weight of said compounds, the oxypropylene to oxyethylene ratio of said total weight being from 0.85:1 to 2.75:1; and wherein said surfactant (b) are ethoxylates of a mixture of alcohols having the formula:

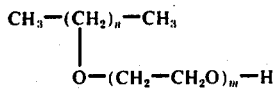

where $n$ is in the range from 9 to 13 and $m$ is an average of 3 to 12; and said dye is present in said composition in an amount ranging from about 0.1 to 15 parts, per 100 parts, by weight, of said surfactant, said composition being substantially non-flammable.

4. A method as defined in claim 3, wherein R in said surfactant (a) can have from 12 to 18 carbon atoms, and the total number of A groups can range from about 4 to about 14; and wherein in surfactant (b) the linear alkyl hydrophobic portion of said surfactant is a mixture of $C_{11}$ to $C_{15}$ linear chains, and the hydrophilic portion of said surfactant is a polyoxyethylene chain randomly attached to the linear alkyl hydrophobic chains through an ether linkage, and wherein said surfactant (b) is selected from the group consisting of said ethoxylates of said mixture of alcohols, wherein $n$ ranges from 9 to 13, and $m$ is an average of 3, 5, 7, 9 or 12.

5. A method as defined in claim 4, wherein said first surfactant in said dye penetrant composition is said surfactant (a), the total number of said oxyethylene and oxypropylene groups A ranging from about 4 to about 8, and wherein said second surfactant in said emulsifier is said surfactant (a), the total number of said oxyethylene and oxypropylene groups A in said last mentioned surfactant ranging from about 9 to about 14.

6. A method as defined in claim 4, wherein said first surfactant in said dye penetrant composition is said surfactant (b), and wherein $m$ is an average of 3 to 4, and wherein said surfactant in said emulsifier is said surfactant (b), wherein m is an average of about 5 to 12.

7. A method as defined in claim 6, wherein $m$ in said first surfactant is an average of 3, and $m$ in said second surfactant is an average of 5, 7, 9 or 12.

8. A method as defined in claim 7, wherein said second surfactant (b) in said emulsifier is a combination of two or more said ethoxylates.

9. A method as defined in claim 8, wherein said surfactant (b) in said emulsifier is a combination of said ethoxylates wherein $m$ is 5 and $m$ is 9.

10. A method as defined in claim 1, wherein said dye is a fluorescent dye and said surface of said object is viewed under fluorescigenous light to obtain colored fluorescent traces from the dye in said cracks and flaws.

11. A method as defined in claim 7, wherein said dye is a fluorescent dye and said surface of said object is viewed under fluorescigenous light to obtain colored fluorescent traces from the dye in said cracks and flaws.

12. A method as defined in claim 1, including applying a developer to said surface after removing said dye penetrant composition from said surface and prior to said viewing the surface of said object.

13. A method as defined in claim 6, including applying a developer to said surface after removing said dye penetrant composition from said surface and prior to said viewing the surface of said object.

14. A postemulsifiable dye penetrant inspection method for detecting cracks and flaws in the surface of an object which comprises applying to said surface a biodegradable liquid dye penetrant composition which consists essentially of (1) a first nonionic biodegradable surfactant in the form of ethoxylates of a mixture of linear secondary aliphatic alcohols having the formula:

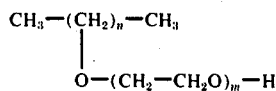

where $n$ is in the range from 9 to 13 and $m$ is an average of 3, the hydrophilic portion of said surfactant being a polyoxyethylene chain randomly attached to the linear alkyl hyrophobic chains through an ether linkage, and (2) a small amount of a fluorescent dye soluble in said surfactant, contacting the surface of said object covered with said dye penetrant with an emulsifier containing as essential component a second nonionic biodegradable surfactant in the form of ethoxylates of a mixture of linear secondary aliphatic alcohols having the general formula set forth above, and where n is in the range from 9 to 13 and $m$ is an average of 5, 7, 9 or 12, and rendering the resulting emulsified dye penetrant composition water soluble, contacting the emulsified penetrant on the surface of said object with water and washing said dye penetrant from said surface without removing said dye penetrant composition from said cracks and flaws in said surface, and viewing the surface of said object under fluorescigenous light to obtain colored fluorescent traces from the dye in said cracks and flaws.

15. A method as defined in claim 14, said dye being present in said dye penetrant composition in an amount ranging from about 0.1 to 15 parts per 100 parts, by weight, of said first surfactant.

16. A method as defined in claim 15, wherein said dye penetrant covered surface of said object is immersed in said emulsifier for a short period, and wherein the emulsified penetrant is sprayed with water for removal thereof, and the object surface dried by air blasting.

17. A method as defined in claim 15, including applying a developer to said object surface after removing said emulsified dye penetrant composition from said surface and prior to said viewing the surface of said object.

18. A method as defined in claim 16, including applying a developer to said object surface after removing said emulsified dye penetrant composition from said surface, and removing excess developer, prior to said viewing the surface of said object.

19. A method as defined in claim 15, wherein said fluorescent dye in said dye penetrant composition is present in an amount ranging from about 0.5 to about 10 parts, per 100 parts, by weight, of said first surfactant.

* * * * *